United States Patent [19]

Dairaku et al.

[11] 4,257,257
[45] Mar. 24, 1981

[54] METHOD AND APPARATUS FOR MEASURING CONCENTRATIONS OF GASEOUS OR VOLATILE SUBSTANCES IN LIQUIDS

[75] Inventors: Kazuo Dairaku; Kazuo Kuki, both of Kobe, Japan

[73] Assignee: Kanegafuchi Kagaku Kogyo Kabushiki Kaisha, Osaka, Japan

[21] Appl. No.: 961,945

[22] Filed: Nov. 20, 1978

[30] Foreign Application Priority Data

Mar. 13, 1978 [JP] Japan ................................. 53-28817
Mar. 16, 1978 [JP] Japan ................................. 53-30656
Mar. 31, 1978 [JP] Japan ................................. 53-38458
Jul. 13, 1978 [JP] Japan ................................. 53-85721
Jul. 17, 1978 [JP] Japan ............................ 53-98489[U]

[51] Int. Cl.$^3$ ............................................. G01N 7/10
[52] U.S. Cl. ........................................ 73/19; 55/158
[58] Field of Search ............................. 73/19; 55/158

[56] References Cited

U.S. PATENT DOCUMENTS

| 3,438,241 | 4/1969 | McKinley, Jr. ........................ 73/19 X |
| 3,567,666 | 3/1971 | Berger ..................................... 55/158 |
| 3,866,460 | 2/1975 | Pearce, Jr. ............................. 73/19 |
| 4,032,309 | 6/1977 | Salemme ................................. 55/158 |

OTHER PUBLICATIONS

"Measurement of Dissolved Oxygen in Fermentations", by D. H. Phillips and M. J. Johnson, Journal of Biochemical and Microbiological Tech. & Engr., vol. III, No. 3, pp. 261-275 (1961).
"Studies of the Measurement of Dissolved Oxygen in Fermentation by Tubing Method", by Cheng-Ching Chen, Journal of Chinese Inst. of Chem. Engrs., 1970, vol. 1, pp. 55-64.
"Desorption of Carbon Dioxide from Fermentation Broth", by H. Yagi and F. Yoshida, Biotechnology and Bioengineering, vol. XIX, pp. 801-819 (1977).

Primary Examiner—Charles A. Ruehl
Attorney, Agent, or Firm—Armstrong, Nikaido, Marmelstein & Kubovcik

[57] ABSTRACT

A carrier gas is passed through a liquid-repellent porous partition tubing having channels extending through the wall of the tubing and immersed in the liquid to be tested, causing a gaseous or volatile substance to permeate through the wall and diffuse into the carrier gas in the tubing. The carrier gas flowing out from the outlet of the tubing and containing a quantity of the substance in equilibrium with the liquid phase is led to a detector connected to the outlet, whereby the concentration of the gaseous or volatile substance in the liquid can be detected continuously or intermittently with high efficiency. The tubing, which is liquid-repellent, prevents ingress of the liquid into the channels but permits the gaseous or volatile substance to diffuse into the carrier gas through a gas layer in the channels at an exceedingly high velocity, thus affording measurements with a short response time. The disclosed method and apparatus are very useful for fermentation processes, brewing processes, cultivation of microorganisms, treatment of fluid oils and fats, and disposal of industrial waste water and are also amenable to the automatic control of such processes.

25 Claims, 19 Drawing Figures

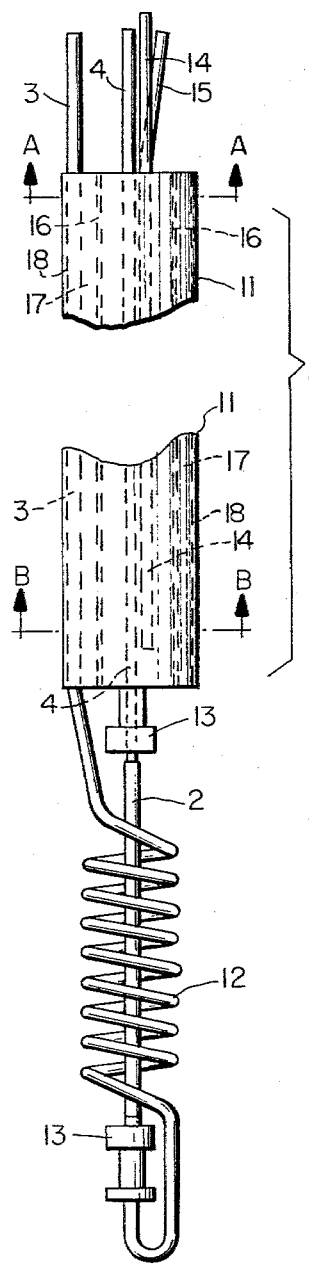
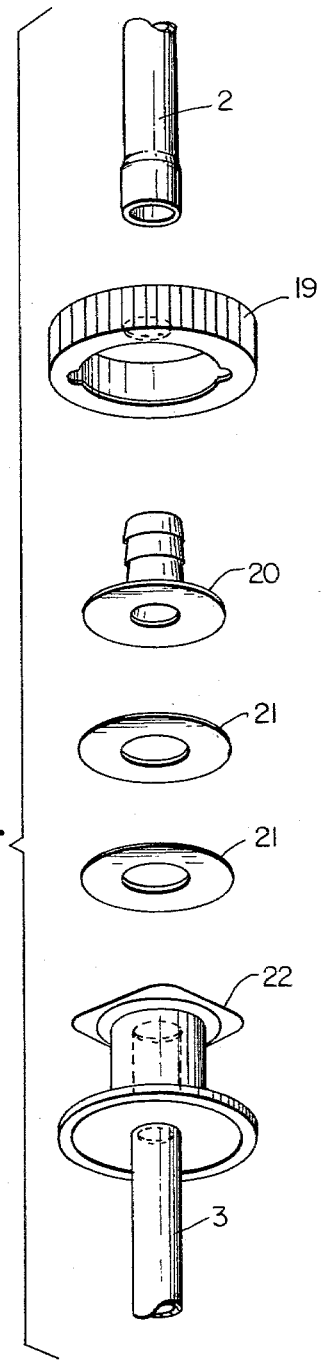
FIG. 12
FIG. 15

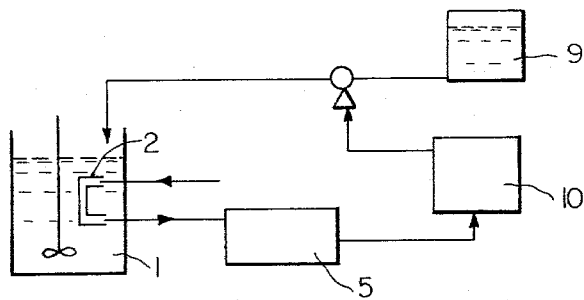
FIG. 17
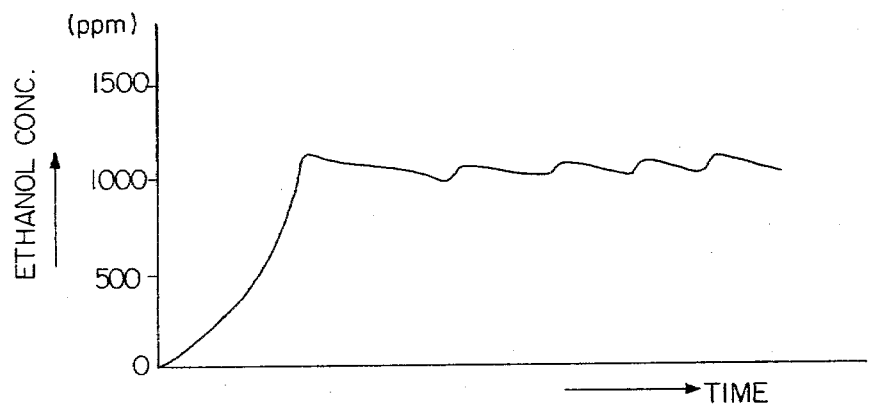
FIG. 18
FIG. 19

METHOD AND APPARATUS FOR MEASURING CONCENTRATIONS OF GASEOUS OR VOLATILE SUBSTANCES IN LIQUIDS

The present invention relates to a novel method of rapidly accurately measuring the concentrations of gaseous or volatile substances in liquids, and also to apparatus therefor.

Various methods are known of detecting or determining gaseous or volatile substances dispersed or dissolved in aqueous liquids such as culture broths, fermented alcoholic mixtures, industrial waste water and suspensions of polymers and oligomers, and also in nonaqueous liquids such as fluid oils or fats. Conventional methods, however, involve problems with respect to the measuring time, apparatus and procedure required as well as the accuracy of the result.

In industries involving alcoholic fermentation for beverages, the concentration of alcohol (predominantly of ethanol) is determined generally by distilling off an alcoholic aqueous solution from the sample and measuring the specific gravity of the solution at a specified standard temperature (e.g. at 15° C. for sake) in terms of Baumè degree or sake meter value. The concentration thus determined is utilized for process control or is used as a standard value in trade or for certification.

This method nevertheless gives different values of specific gravity even at the same concentration of alcohol when the solution is not tested accurately at the standard temperature. Similarly beverages of the same alcohol concentration but different kinds will vary in specific gravity owing to the presence of particular acid, essence, sugar and like components other than alcohol which are characteristic of each beverage. This gives rise to the necessity of correcting the specific gravity value obtained to compensate for the deviation in the temperature or difference in the kind of beverage. Thus extreme difficulty is usually encountered in determining accurate alcohol concentrations when variations are involved in conditions such as temperature and the concentration of some component other than alcohol.

Simplified methods have also been proposed. They include a method in which a reagent is used for leaching out alcohol only, another method which utilizes viscosity, and still another method which employs a reflactometer, but these methods have not found wide use because of various drawbacks.

Other methods heretofore known are those which require a distillation procedure, such as the indirect method, the ebullioscopic method, a method in which the alcohol concentration of a solution is calculated from the specific gravity values of a sample before and after the removal of alcohol from the sample by distillation, and another method in which the sample is oxidized with a solution of potassium bichromate and thereafter titrated. However, each of such methods has difficulty in obtaining many items of data within a short period of time since a sophisticated technique and a special apparatus are essential to the distillation procedure in addition to a skilled analyst. Further according to these methods, measurements are obtained by intermittently sampling the solution to be tested and analyzing the samples, so that when the state of the solution alters with time, the samples do not always display the state that is typical of the solution. Additionally it is in no way possible for the above-mentioned methods to continuously measure and indicate variations in the alcohol concentration of the test solution with the lapse of time.

With culture systems for microorganisms, it is essential to the control of culture to measure the concentrations or variations in the concentrations of main carbon source, micronutrients and metabolites, which are generally gaseous or volatile substances such as alcohols, ketones, organic acids and lower hydrocarbons. In fact, the control of the culture system based on the concentrations or variations in the concentrations of these substances contained in the culture broth is commercially of extreme importance in ensuring an increased yield and improved uniform quality. For this purpose, therefore, it has been strongly desired to develop a method of efficiently accurately measuring concentrations of these gaseous or volatile substances in culture broths for microorganisms.

However, great difficulties have heretofore been experienced in accurately and rapidly or continuously measuring the concentrations of important factors in culture broths containing microorganisms and like solids. The concentration of the contemplated substance is usually measured for example by removing solids from the sample as by centrifuging or filtration and analyzing a specified quantity of the resulting supernatant as by gas chromatography. This method has the drawback that the measurement takes about 20 minutes after sampling and requires a manual procedure. The above method, even when adapted for automatic maintenance of culture systems of microorganisms, still involves a delay of about 15 minutes in response and requires a very complex sampler including, for example, a device for removing solids. The method is therefore very disadvantageous in respect of equipment cost and operation. Accordingly for the automatic control of such culture systems, gas analysis which permits easy sampling and measurement is generally employed to use the resulting value as the control factor. For instance, it is attempted to measure the concentration of ethanol in the gas evolved from the system to estimate the ethanol concentration of the culture broth and to control the culture broth concentration based on the estimated value. It is also known to measure the concentrations of $CO_2$ and $O_2$ in the gas evolved, calculate the respiratory quotient RQ (RQ=the quantity of $CO_2$ evolved/the quantity of $O_2$ absorbed) and control the feed of the main carbon source based on the value obtained (Japanese Patent Application Disclosure No. 125686/1977). However, these methods still have problems in respect of the speed of response and accuracy of measurement since the quantity of gas evolved from the broth is indirectly measured in a gas phase which contains a large quantity of inert gas supply.

It has therefore been desired to provide a method by which the concentration of the main carbon source or metabolite in the culture broth can be directly measured with ease so that the culture system can be controlled commercially advantageously based on the measurements or values calculated from the measurements.

Another method has recently been proposed in which air is passed at a given rate through a silicone rubber tube immersed in a culture broth, and the methanol (main carbon source) permeating through the tube wall is detected by gas chromatograph to measure the methanol concentration of the culture broth. The concentration of the main carbon source in the culture broth can be measured by this relatively simple method, but the wall of the silicone rubber tube has much higher resistance than the porous partition tubing of this invention against the permeation of a gaseous or volatile substance, with the result that variations in the methanol concentration of the broth are detected with a response delay of about 10 to 20 minutes. The method therefore still remains to be improved for the control of culture systems.

In the oil or fat deodorizing process for purification in the oil and fat industry, oil or fat is usually heated with a hot heat medium within a deodorizer until the concentration of the odorous volatile component has been reduced to a specified level and is thereafter fed to the subsequent process. This treatment is generally conducted batchwise or semi-batchwise, but since there is no commercially useful method of detecting the desired reduction in the concentration of the odorous substance, the result of the treatment is checked by withdrawing part of the treated product, cooling the product to a suitable temperature and examining the cooled product for odor mainly by a sensory evaluation. Accordingly when the process is carried out under strict control, the deodorized product is retained in the apparatus until the sensory evaluation is completed. This entails a seriously reduced efficiency. To reduce the time loss and render the apparatus operable with an enhanced efficiency, the sensory evaluation must be replaced by a method of accurately rapidly measuring the concentrations of odorous volatile substances in oils and fats.

Directing attention to the foregoing problems, we have conducted intensive research on a method of rapidly, accurately and continuously measuring the concentrations of gaseous or volatile substances in liquids and accomplished this invention, which will be described below in greater detail with reference to the accompanying drawings, in which:

FIG. 12 is a view showing another apparatus embodying the invention;

FIG. 15 is an exploded view showing a joint for a tube of the cartridge type for use in the apparatus of the invention;

FIG. 17 is a diagram showing the apparatus used in Example 5; and

FIGS. 18 and 19 are diagrams showing the results achieved in Example 5.

Figure 1:
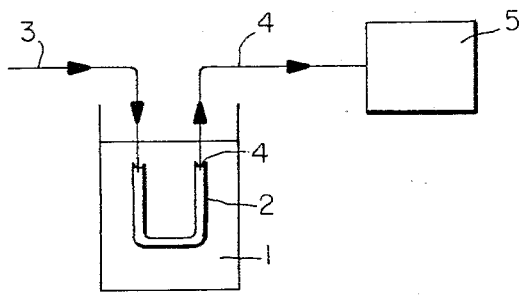
FIG. 1 is a diagram showing the principle of the method of this invention.

The method of this invention will be described first in detail.

Briefly the method of this invention for measuring the concentration of a gaseous or volatile substance in a liquid comprises the steps of immersing in the liquid a liquid-repellent porous partition tubing having channels extending through the wall of the tubing, passing a carrier gas through the partition tubing, leading the carrier gas to a detector and detecting the quantity of the gaseous or volatile substance permeating through the tubing wall from the liquid and diffusing into the carrier gas to continuously or intermittently measure the concentration of the substance in the liquid.

The porous partition tubing to be used in this invention must be liquid-repellent and have minute channels extending through the wall of the tubing. Examples of materials useful for forming such tubing are synthetic resins including ethylene tetrafluoride resin and like ethylene halide resins, vinylidene halide resin, polypropylene resin, polyester resin, and polyvinyl chloride resin and like vinyl halide resins, among which ethylene tetrafluoride resin is especially preferable to use. The tubing may be made by giving liquid-repellency to porous materials with no liquid-repellency.

The tubing of this invention may be circular, elliptical, quadrilateral or of any shape in cross section provided that it is a suitably shaped hollow body meeting the conditions required for use in respect of surface area and strength. Tubes useful in this invention of course include those having in part of the periphery thereof a liquid-repellent porous partition sheet having minute channels extending therethrough.

Examples of useful carrier gases are nitrogen and helium which are usually used. Air is usable depending on the type of the detector used.

The carrier gas is passed through the tubing preferably at constant pressure and at a constant flow rate. With use of a tube several millimeters in inside diameter, for example, the flow of the carrier gas is maintained preferably at a constant rate of about 40 to about 80 c.c./min. It is also desired that the carrier gas be maintained at the same temperature as the liquid to be tested. The pressure of the carrier gas can be equal to, higher than or lower than the liquid, although excessively high pressure is objectionable since the gas will then jet out into the liquid through the minute channels of the porous wall. Thus the carrier gas, when used under increased pressure, should have such pressure that it will not discharge through the channels into the liquid. Conversely when the carrier gas is used at lower pressure than the liquid to be tested, the pressure difference should be such that the liquid will not seep through the channels into the interior or will not deform the tubing. A marked pressure difference, if present, should be reduced to a predetermined value by a carrier gas pressure regulating device.

Since the pressure drop of the gas through the tubing should be small, the tubing may preferably have an inside diameter of 2 to 8 mm. When having too small a diameter, however, the tubing will locally permit an excessive rise in pressure, possibly allowing an outflow of the gas through the tube wall. The optimum diameter must therefore be determined within the range that will not result in such an objection. The wall of the partition tubing, which must withstand some pressure difference, is preferably about 200 to 1,000 μm in thickness. A larger wall thickness would reduce the speed of diffusion of the gaseous or volatile substance through the wall. The tubing must have such a length that an equilibrium will be established between the concentration of the gaseous or volatile substance in the carrier gas and the concentration of the substance in the liquid to be tested. Stated more specifically the length of the tubing, L, needs to be such that $C/C*$ given by the following equation is approximately 1.0.

$$C/C* = 1.0 - \exp(-\pi KDL/Q) \quad (1)$$

where C is the concentration of the gaseous or volatile substance at the outlet of the tubing, $C*$ is the concentration of the same at equilibrium, D is the inside diameter of the tubing, K is the overall radial mass-transfer coefficient of the substance, and Q is the flow rate of the carrier gas.

Figure 5:
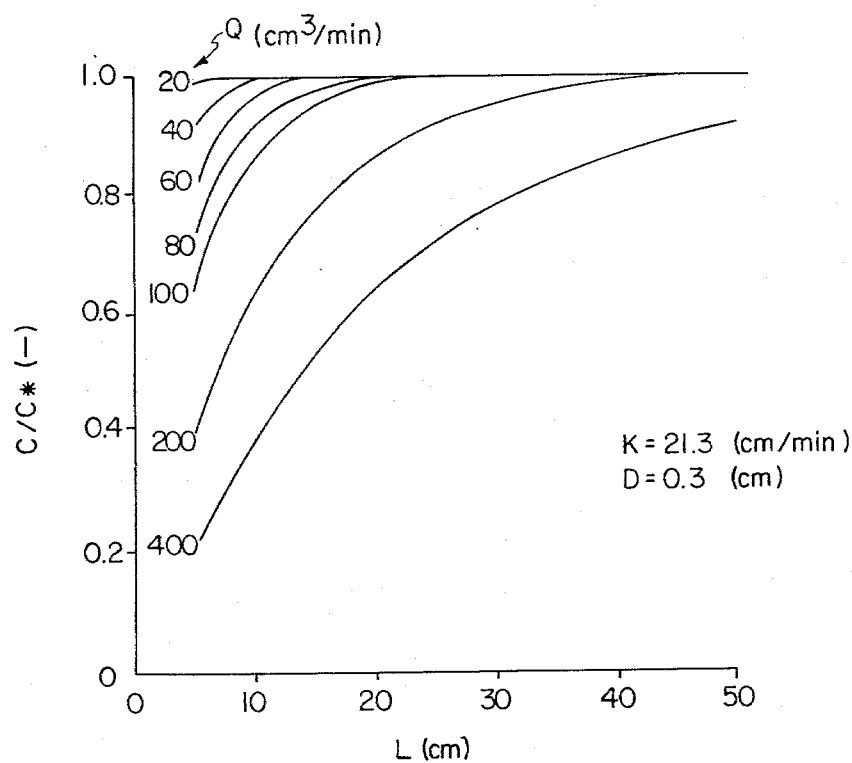
FIG. 5 is a graph showing the relation of the length of tubing with the concentration of gaseous or volatile substance at the outlet of the tubing and with the flow of a carrier gas.

FIG. 5 is a graph illustrating this relation. With the flow of the carrier gas usually at a rate of about 20 to about 80 c.c./min., the concentration of the substance at the outlet is in equilibrium if the tubing has a length of 10 to 30 cm. Porous bodies now commercially available in pore sizes of 0.1 to 5 μm are all usable. Those larger than 5 μm or smaller than 0.1 μm in pore size are also satisfactorily usable under selected conditions. To be more specific, the material, pore size, etc. of the porous partition to be used may be determined based on the following relation and in accordance with the measuring conditions.

The method of this invention becomes infeasible when the liquid to be tested permeates the porous wall through the minute channels. The pressure difference $\Delta P$ at which the liquid starts to permeate through the channels is dependent on the material of the porous partition, the contact angle $\theta$ between the liquid and the material, the interfacial tension therebetween and the pore size as defined by the following equation (2). The material and pore size may be determined with further consideration given to the shape of the channel.

$$P = \frac{2\gamma \cdot \cos \theta}{R} \quad (2)$$

wherein R is the radius of the pore.

The detector is preferably a gas chromatograph. When the carrier gas passed through the tubing contains a plurality of gaseous or volatile substances, the gas is sampled by a gas sampler, each sample is separated by a column and the separated portions are fed to detectors individually for measurement. When the carrier gas passed through the tubing contains a substantially single substance, the carrier gas is fed directly to a flame ionization detector continuously for measurement without the necessity of separating the gas by a column. The latter method, which does not use any column or gas sampler, is mechanically simple and useful for automatic control since the data is continuously obtained. When the error of measurements occurs due to temperature variation of the liquid and further high accuracy is needed, the error should be corrected by a suitable temperature compensating device.

The present method afforded measurements with extremely high accuracy, for example, of ±0.6% in terms of error when determining the concentration of 40% ethanol-water solution with use of a flame ionization detector (Model GC-6A, product of Shimadzu Co., Ltd., Japan).

Figure 6:
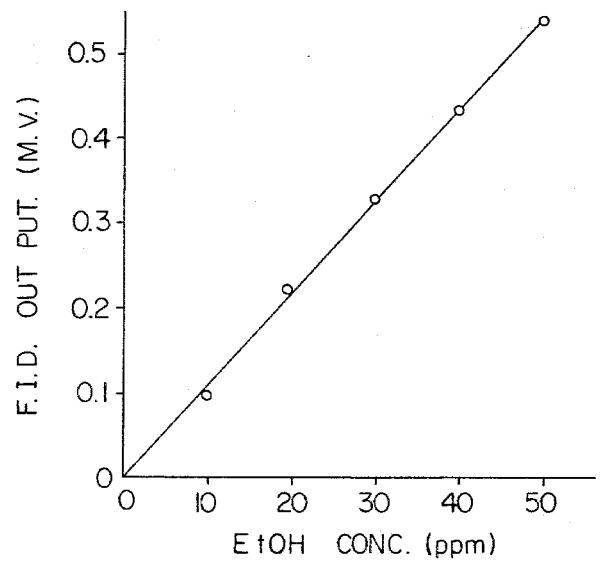
FIG. 6 is a graph showing the relation between the output of the detector and the concentration of ethanol in a low-concentration range.
Figure 7:
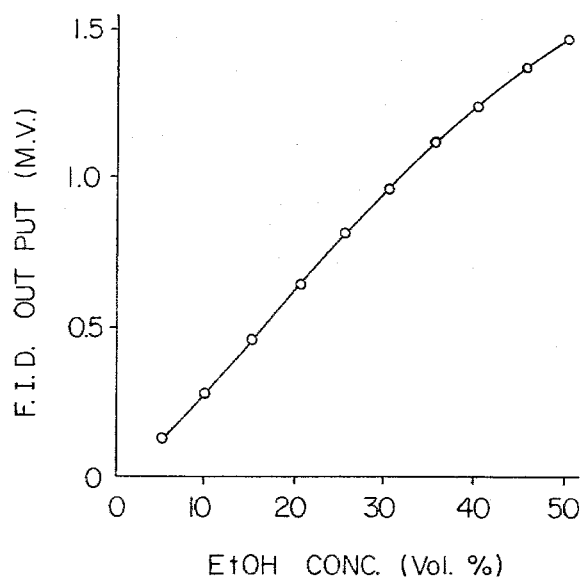
FIG. 7 is a graph showing the relation between the output of the detector and the concentration of ethanol in a high-concentration range.

When the method was practiced on water-ethanol systems with use of an ethylene tetrafluoride resin porous tube (1.0 μm in pore size, 60% in porosity, 0.5 mm in wall thickness, 3 mm in inside diameter and 10 cm in length) and a flame ionization detector, the relation between the ethanol concentration and the detector output was found to be rectilinear in a low-concentration range of the order of 10 ppm as seen in FIG. 6 and to be in accordance with the gas-liquid equilibrium relation in a high-concentration range of the order of 10% as shown in FIG. 7.

The range of measurable low concentrations is limited to the order of 10 ppm in view of the ability of presently available flame ionization detectors which are desirable for use in this invention. In the range of high ethanol concentrations exceeding 50%, the solution under test has reduced interfacial tension and becomes more likely to ingress into the minute channels of the tubing. At concentrations higher than 90%, the tubing no longer functions as a porous partition. This method, however, is practically enough to apply in brewing industry for measuring alcohol concentration of products like sake, whisky, wine, etc, attributed to the applicability in high concentration range. When measuring ethanol concentrations, the present method can be practiced advantageously at concentrations of up to 90%, more advantageously at concentrations of up to 50%, as seen in FIG. 7.

The present invention is characterized by sampling a gaseous or volatile substance from a liquid in the form of a gas which is easily determinable with simple means, namely with a liquid-repellent porous partition tubing having minute channels extending through the wall of the tubing and measuring the concentration of the substance continuously or intermittently with high efficiency and high accuracy by known analyzer preferably by gas chromatograph.

Tubing method using silicone rubber tubing is already known as mentioned above. However, with silicone rubber tubing, the gaseous or volatile substance in the test liquid dissolves in and diffuses through the solid wall of the tubing into the carrier gas in the tubing, whereas with the porous tubing of this invention, the gaseous or volatile substance permeates through the minute channels of the porous tubing and diffuses into the carrier gas inside the tubing. Thus the mode of diffusion through the former tubing entirely differs from that through the latter. Additionally the speed of diffusion through the latter is exceedingly higher than that of diffusion through the former.

The speed of diffusion of gaseous or volatile substances through a liquid-repellent porous partition into a gaseous phase is given by:

$$J_A = \frac{mCX_A}{RT\left(\frac{mS_L}{RTD_L} + \frac{CS_G}{HD_G}\right)} \quad (3)$$

The denominator of the equation (3), corresponding to the resistance against diffusion, comprises two elements: the resistance encountered in the boundary film on the liquid side and defined by the first term, and the resistance to the passage of the substance through minute channels of the porous tubing given by the second term.

Generally the second term is much smaller than the first term. The combined resistance of the two is governed predominantly by the first term, namely by the resistance involved in the boundary film on the liquid side.

With the silicone rubber tubing, on the other hand, the resistance against the diffusion of a gaseous or volatile substance through the wall of the tubing is generally much higher than the resistance in the boundary film on the liquid side. Consequently the speed of diffusion through the liquid-repellent porous tubing in which the resistance of the boundary film against diffusion predominates is higher than in the case of the silicone rubber tubing in which the resistance of the tubing wall against dissolving and diffusion predominates. Experimental comparison between the two in respect of overall radial mass-transfer coefficient has revealed that the silicone rubber tubing has about 1/50 of the coefficient of the porous tubing of this invention. In other words, the latter is less resistant to the diffusion than the former and is exceedingly more responsive to variations in the concentration of the gaseous or volatile substance contained in the liquid phase than the former. In fact, the method of this invention which uses tubing having a high diffusion speed gives, for example, 90% responses in about 1 minutes to variations in the concentration of aqueous alcohol solution over a low-concentration range. This speed of response is at least about 10 times higher than that achieved by the use of silicone rubber tubing, hence remarkably superior.

Figure 2:
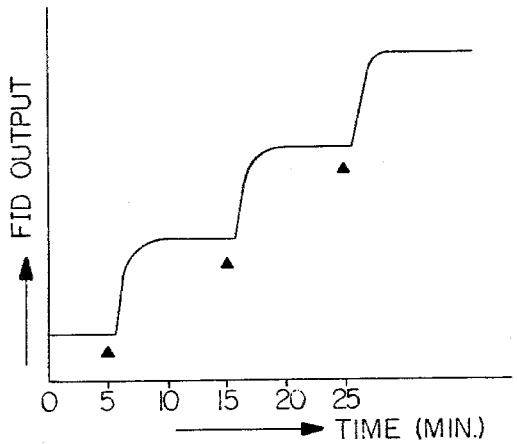
FIG. 2 is a graph showing responses achieved by the method of this invention relative to stepwise variations in the concentration of a gaseous or volatile substance in the liquid tested.
Figure 3:
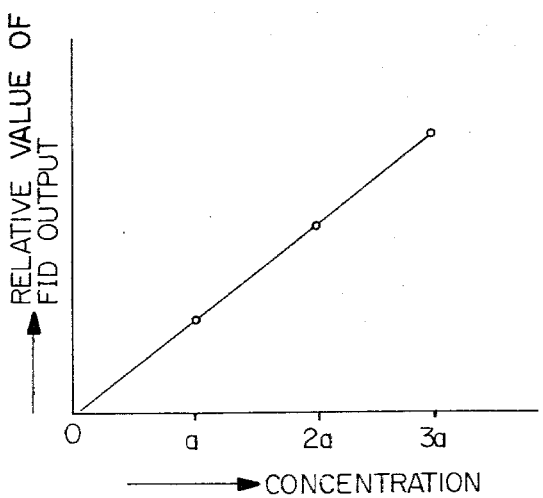
FIG. 3 is a graph showing the relation between the concentration of the gaseous or volatile substance and the output (peak level) of a detector.

The method of this invention will be further described with reference to FIGS. 1 to 3. The principle of the present method is illustrated in FIG. 1, which shows the liquid 1 to be tested and containing a gaseous or volatile substance, a liquid-repellent porous partition tubing 2, a carrier gas supply pipe 3, a carrier gas discharge pipe 4 and a detector 5. FIGS. 2 and 3 correspond to Examples 1 to 3. FIG. 2 is a graph showing the response characteristics of the method of this invention relative to stepwise variations in the concentration of a gaseous or volatile substance in the liquid tested. FIG. 3 is a graph showing the relation between the concentration of the gaseous or volatile substance and the output (peak level) of a flame ionization detector. Stated more specifically, the present method was found highly responsive in that it afforded 90% responses in about 2 minutes to stepwise variations in the concentration of ethanol (in the range of 0 to 1,500 ppm) in the culture broth of Example 1 (FIG. 2). There was a rectilinear relation between the ethanol concentration of the culture broth and the output of the detector (FIG. 3). The present method achieved 90% responses in 3 minutes to stepwise variations in the concentration of phenol in the aqueous solution of Example 2 (over the concentration range of 0 to 50 ppm), with a rectilinear relation established between the phenol concentration and the detector output. The method further provided 90% responses in about 2 minutes to stepwise variations in the concentration of hexane in the rice oil of Example 3 (over the concentration range of 0 to 400 ppm), with a rectilinear relation similarly established between the hexane concentration and the detector output. These results indicate that the present method is exceedingly more responsive than conventional methods, although the time required for responses to stepwise variations in concentration varies with the measuring conditions involved. The rectilinear relation established between the concentration of the gaseous or volatile substance and the detector output reveals that the present method is fully useful for the quantitative determination of such substances.

The measuring method of this invention is useful for measuring the concentrations of gaseous or volatile substances in aqueous liquids for the automatic control of microorganism culture broths and of the alcohol concentration of fermentation or brewing liquid and for the disposal of industrial waste water. The method is also usable for measuring the concentrations of gaseous or volatile substances in fluid oils and fats. Thus the method finds wide use for the determination of gaseous or volatile substances contained in the liquids to be tested. Further since the present method gives rapid and accurate responses as described above, the method is amenable to automatic process control with use of a computer. When the porous partition tubing is made, for example, of ethylene tetrafluoride resin for uses in which heat resistance against usual thermal sterilization is required or for use with food and pharmaceutical products which must be handled sanitarily, the present method will achieve fully satisfactory results while fulfilling such requirement.

Apparatus for practicing the method of this invention will now be described in detail. Briefly the present invention further provides: (i) an apparatus for sampling a gaseous or volatile substance in a liquid comprising a liquid-repellent porous partition tubing having minute channels extending through the wall of the partition tubing for permitting the gaseous or volatile substance to diffuse therethrough into a carrier gas in the partition tubing, the partition tubing having one end in communication with a carrier gas supply pipe and the other end in communication with a carrier gas discharge pipe extending to means for measuring the concentration of the gaseous or volatile substance; (ii) an apparatus for sampling a gaseous or volatile substance in a liquid comprising a liquid-repellent porous partition tubing having minute channels extending through the wall of the partition tubing for permitting the gaseous or volatile substance to diffuse therethrough into a carrier gas in the partition tubing, the partition tubing having one end in communication with a carrier gas supply pipe and the other end in communication with a carrier gas discharge pipe extending to means for measuring the concentration of the gaseous or volatile substance, the carrier gas discharge pipe being provided with heating means; and (iii) an apparatus for sampling a gaseous or volatile substance in a liquid comprising a liquid-repellent porous partition tubing having minute channels extending through the wall of the partition tubing for permitting the gaseous or volatile substance to diffuse therethrough into a carrier gas in the partition tubing, the tubing having one end in communication with a carrier gas supply pipe and the other end in communication with a carrier gas discharge pipe extending to means for measuring the concentration of the gaseous or volatile substance, the carrier gas supply pipe including a tubular portion to be immersed in the liquid for exchanging heat with the liquid.

Figure 4:
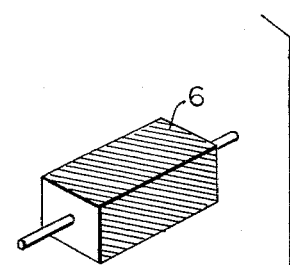
FIG. 4 is a diagram showing tubes of various shapes.
Figure 4:
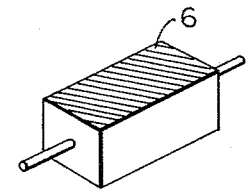
Figure 4:
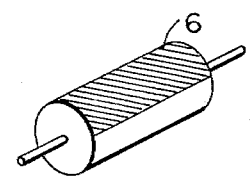
Figure 4:
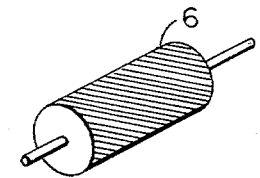
Figure 4:
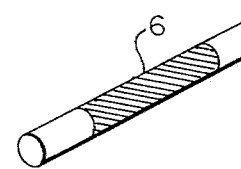

The tubing of this invention may be circular, elliptical, quadrilateral or of any shape in cross section provided that it is a suitably shaped hollow body meeting the conditions required for use in respect of surface area and strength. Tubes useful in this invention of course include those having in part of the periphery thereof a liquid-repellent porous partition sheet having minute channels extending therethrough as indicated at 6 in FIG. 4.

The porous partition tubing to be used in this invention must be liquid-repellent and have minute channels extending through the wall of the tubing. Examples of materials useful for forming such tubing are synthetic resins including ethylene tetrafluoride resin and like ethylene halide resins, vinylidene halide resin, polypropylene resin, polyester resin, and polyvinyl chloride resin and like vinyl halide resins, among which ethylene tetrafluoride resin is especially preferable to use. The tubing may be made by giving liquid-repellency to porous materials with no liquid-repellency.

Since the pressure loss of the gas through the tubing should be small, the tubing may preferably have an inside diameter of 2 to 8 mm. The wall of the partition tubing must withstand some pressure difference, whereas too large a wall thickness would reduce the speed of diffusion of the gaseous or volatile substance through the wall. Thus the tubing is preferably about 200 to about 1,000 $\mu$m in thickness.

When collecting a gaseous or volatile substance from the liquid to be tested with the tubing, a carrier gas is passed through the tubing immersed in the liquid. The volatile substance in the liquid passes through a film of gas formed in the minute channels of the tubing wall to diffuse into the carrier gas to a concentration in equilibrium with the concentration of the substance in the liquid. The carrier gas containing the substance thus diffusing is introduced into a detector. The length of the tubing may be determined by experiments in accordance with the measuring conditions concerned. In the case of tubing having a diameter specified above, satisfactory results can be achieved with 10- to 30-cm-long tubing when the carrier gas is fed at a specified rate. Useful pore sizes for the porous tubing are usually in the range of 0.1 to 5 $\mu$m. Since the pore size is dependent on the interfacial tension and pressure of the liquid, pore sizes larger than 5 $\mu$m or smaller than 0.1 $\mu$m are also acceptable under selected conditions.

With the sampling apparatus of this invention, the partition tubing has one end communicating with a carrier gas supply pipe and the other end communicating with a carrier gas discharge pipe which is connected to means for measuring the concentration of the gaseous or volatile substance, such as gas chromatograph. Preferably the tubing is detachably connected to these pipes, for example, by a joint of the cartridge type as seen in FIG. 15. Such a joint is useful for the replacement or washing of the tubing.

When the carrier gas discharge pipe connecting the tubing to a gas chromatographic device or like measuring means is short, the apparatus of the type (i) described above will fully achieve the contemplated object, but if a long discharge pipe is used, there arises the necessity of providing heating means for the discharge pipe to assure accurate measurement for the reason given below.

When the carrier gas is passed through the porous partition tubing as immersed in the liquid to be tested, the gaseous or volatile substance permeates through the tubing wall and diffuses into the carrier gas in the tubing to a concentration in equilibrium with the concentration of the same substance present in the liquid. Accordingly if a wall area sufficient to establish the equilibrium (as afforded by a tube 3 mm in inside diameter and about 10 to about 30 cm in length), the carrier gas at the outlet of the tubing has the vapor pressure determined by the pressure and temperature of the system concerned and in equilibrium with the liquid. The carrier gas at the outlet is then a saturated gas. However, when the gas is cooled to a temperature lower than the liquid upon flowing out from the tubing into the discharge pipe, part of the saturating vapor of the substance as well as part of water vapor condenses to liquid. For instance, when the ethanol concentration of a yeast cultivating broth is measured, the carrier gas contains water and ethanol vapors in equilibrium at the temperature of the broth (e.g. 33° C.), but if the gas discharge pipe is exposed to the atmosphere, the gas will be cooled approximately to the ambient temperature (e.g. about 20° C.). As a result, the carrier gas through the discharge pipe will contain the quantities of water and ethanol vapors which saturate the gas at 20° C., with portions of the water vapor and ethanol vapor condensed to liquid. If the pipe for the discharge of the carrier gas from the porous tubing is maintained at a temperature not lower than the temperature of the liquid under test, such an objectionable result is avoidable to achieve the contemplated object.

Examples of means useful for this purpose are heating devices provided around the carrier gas discharge pipe, such as a double-wall tubular assembly in which hot water is passed around the carrier gas discharge pipe, a single or a plurality of pipes coextensive with the discharge pipe for passing hot water, an electric heating element such as nichrome wire, or an electric pipe heater. Preferably such a heating device may be covered with a heat insulating material and further with a coating or molding of epoxy, vinyl chloride, propylene or like high polymer resin over the insulator.

The quantity of the gaseous or volatile substance contained in the liquid and permeating through the wall of the porous tubing into the carrier gas therein is in equilibrium with the concentration of the substance present in the liquid at the temperature and pressure involved and is dependently largely on temperature. Accordingly if the carrier gas through the tubing has a temperature much higher or lower than the temperature of the liquid, the quantity of the substance diffusing into the gas in the form of vapor differs from that resulting from an equilibrium. The concentration of the carrier gas, if measured, will not accurately indicate the concentration of the substance in the liquid.

To preclude such improper sampling, the carrier gas supply channel communicating with the porous tubing must be adapted to exchange heat with the liquid for maintaining the carrier gas at the same temperature as the liquid to be tested. Stated more specifically, it is desired that the carrier gas supply pipe be provided with heat exchange means which has appropriate heat transfer coefficient and surface area relative to the flow rate of the carrier gas and which is made preferably of metal. Most desirably the carrier gas supply pipe includes a metal tubular portion of small wall thickness where it is immersed in the test liquid. The tubular portion to be immersed in the liquid may be in a helical or zigzag form or may be provided with heat exchanger ridges or fins so as to be exposed to the liquid over an increased surface area.

Figure 8:
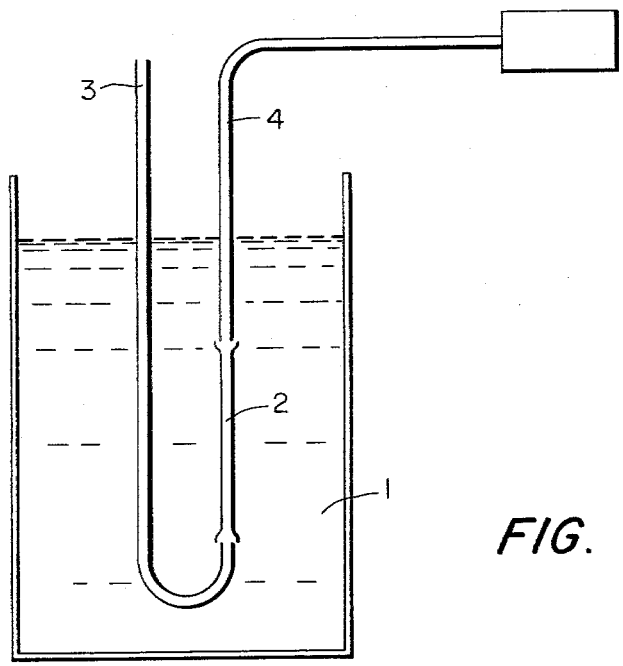
FIGS. 8, 9, 10 and 11 are views schematically showing various apparatus embodying this invention.
Figure 9:
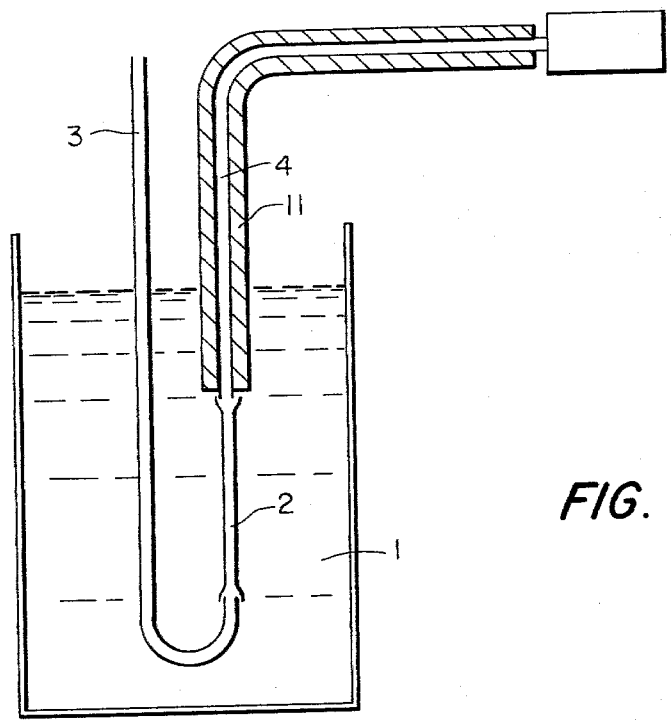
Figure 10:
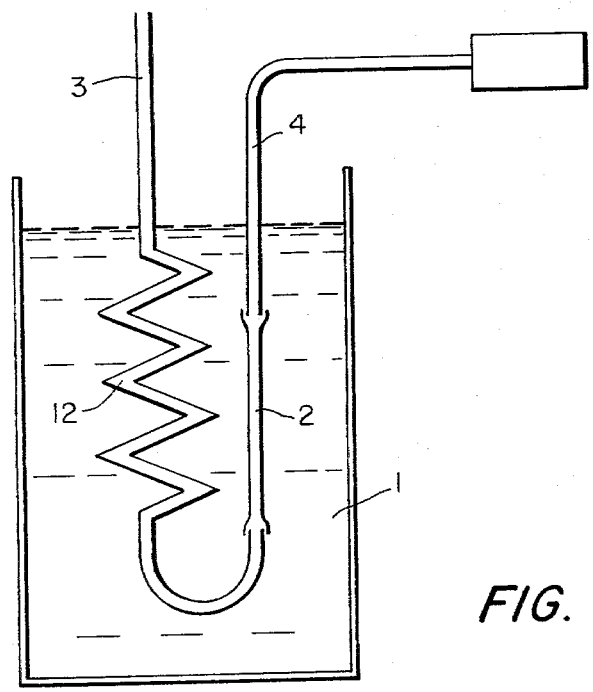
Figure 11:
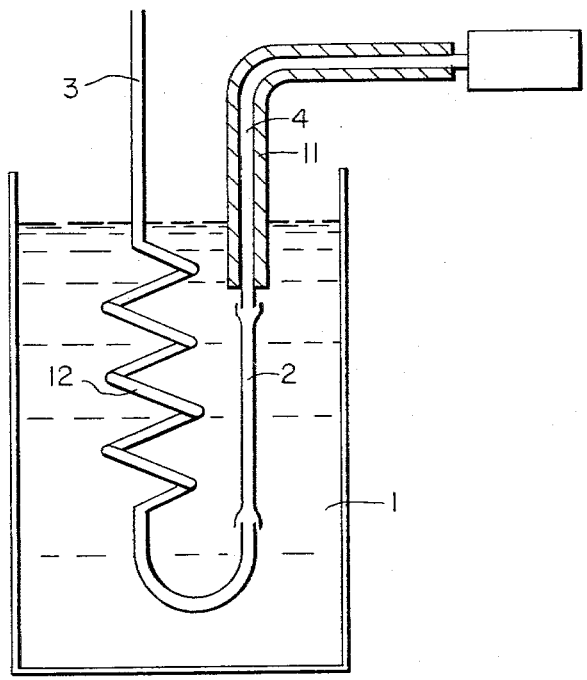
Figure 13:
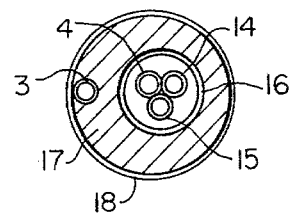
FIG. 13 is a view in section taken along the line A—A in FIG. 12.
Figure 14:
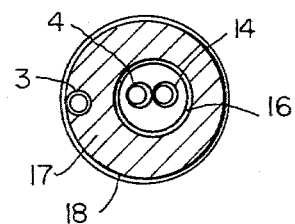
FIG. 14 is a view in section taken along the line B—B in FIG. 12.

FIGS. 8 to 11 are diagrams schematically showing various embodiments of the present invention. Throughout these drawings and others showing the principle or embodiments of the invention, like parts are referred to by like reference numerals. FIG. 8 shows an apparatus adapted for uses in which the carrier gas supply channel and discharge channel need not be provided with any heat exchange means. The apparatus comprises a liquid-repellent porous partition tubing 2, a carrier gas supply pipe 3 and a carrier gas discharge pipe 4. Indicated at 1 is the liquid to be tested. FIG. 9 shows an apparatus having the same construction as the apparatus shown in FIG. 8 except that the carrier gas discharge pipe 4 is provided with a heating device 11 (for effecting heat exchange). FIG. 10 shows another apparatus having the same construction as the apparatus of FIG. 8 except that the carrier gas supply pipe 3 includes a zigzag tubular portion 12 for exchanging heat with the liquid 1. The apparatus shown in FIG. 11 is similar to the above embodiments except that the carrier gas supply pipe 3 and the carrier gas discharge pipe 4 have a helical tubular portion 12 and a heating device 11 respectively. FIGS. 12 to 14 show another apparatus of this invention comprising a liquid-repellent porous partition tubing 2, a carrier gas supply pipe 3, a carrier gas discharge pipe 4, a heating device 11, a tubular portion 12 extending helically around the tubing 2, and joints 13 for connecting the opposite ends of the tubing 2 to the pipes 3 and 4. The heating device 11 comprises a bottomed tubular member 16 through which the discharge pipe 4 extends, a hot water inlet duct 14 extending into the tubular member 16 toward its bottom, a water outlet duct 15 extending into the upper end of the tubular member 16, a heat insulator 17 provided around the tubular member 16 and a resin layer 18 covering the insulator 17. The carrier gas supply pipe 3 extends through the insulator 17. With this embodiment, carrier gas is supplied through the pipe 3, subjected to heat exchange with the liquid to be tested while flowing through the helical tubular portion 12 immersed in the liquid, and then passed through the tubing 2. The carrier gas containing a gaseous or volatile substance diffusing through the wall of the tubing 2 into the gas then passes through the discharge pipe 4 while being heated and is led to a detector. The gas is heated with the hot water supplied through the inlet duct 14 and run off from the outlet duct 15.

FIG. 15 shows the aforementioned joint of the cartridge type. The joint comprises a fastening member 19, a holder 20, packings 21 and a receiving member 22. A porous partition tubing 2 is connected to a carrier gas supply pipe 3 by the joint.

The present invention will become more apparent from the following examples, which however are given for illustrative purposes only and are in no way limitative.

EXAMPLE 1

For the determination of a gaseous or volatile substance in a culture broth, the following cultivation experiment was conducted. The ethanol concentration of the culture broth was measured.

Strain used:
*Saccharomyces cerevisiae* (baker's yeast)
Main carbon source and nutrients:
30% Glucose as the main carbon source and the following nutrients.

| | | | | |
|---|---|---|---|---|
| $H_3PO_4$ | 4,000 ppm | $FeSO_4 \cdot 7H_2O$ | 200 ppm | |
| KCl | 4,000 | $ZnSO_4 \cdot 7H_2O$ | 200 | |
| $MgSO_4$ | 4,000 | $MnSO_4 \cdot 6H_2O$ | 20 | |
| Ammonium sulfate | 500 | $CuSO_4 \cdot 6H_2O$ | 4 | |
| NaCl | 100 | Vitamin Mixture | 150 | |
| $CaCl_2$ | 200 | Yeast Extract | 1,000 | |

Culture conditions:

The yeast was cultured in a 30-liter jar fermenter with the broth adjusted to a temperature of 33° C. and to a pH of 4.5 with use of an aqueous solution of ammonia. Air was supplied at a rate of 20 Nl/min with stirring at 500 r.p.m. The glucose was added by the exponential fed-batch method after placing the nutrients into the fermenter. The initial solids concentration was 1% by dry weight.

Although the yeast inherently produces ethanol in the culture broth as a metabolite, predetermined quantities of ethanol were added intermittently every 5 minutes to check the detector for responses to stepwise variations in the ethanol concentration.

Measuring method:

According to the principle shown in FIG. 1, a partition tube was used which comprised a box-shaped container made of SUS (stainless steel) and a porous partition sheet attached to one open side of the container, the sheet having minute channels extending therethrough. A carrier gas was introduced into the tube at its one end, run off from the other end thereof and led to a flame ionization detector. The output of the detector was continuously recorded. The tubing device was immersed in the culture broth in the jar fermenter.

The porous sheet, made of ethylene tetrafluoride resin, measured 2.0 cm × 12.0 cm and had an area of 24.0 $cm^2$, a thickness of 0.55 mm, a maximum pore size of 2.0 $\mu m$ and a a porosity of 62%. Nitrogen gas used as the carrier gas was passed through the tube at a flow rate of 60 c.c./min.

The experiment produced highly responsive results, affording 90% responses in about 2 minutes to stepwise variations in the ethanol concentration of the culture broth as shown in FIG. 2. A rectilinear relation was found between the ethanol concentration of the culture broth and the output of the detector as shown in FIG. 3 in which a=500 ppm. The method is therefore fully useful for quantitative determination.

EXAMPLE 2

The following experiment was conducted according to the principle shown in FIG. 1. A water-repellent porous tube was immersed in a beaker containing 500 c.c. of pure water. Nitrogen gas was passed through the tube as a carrier gas and led to a flame ionization detector (FID), the output of which was continuously recorded. While maintaining the water in the beaker at a constant temperature of 25° C., a specified quantity of an aqueous phenol solution diluted to a concentration of 17.1 ppm was added dropwise to the water three times at a given time interval with vigorous agitation by a magnetic stirrer. The tube was made of ethylene tetrafluoride resin and had an inside diameter of 3.6 mm, a wall thickness of 0.55 mm, a maximum pore size of 1.8 $\mu m$, a porosity of 61.8% and a length of 25 cm. The carrier gas was fed at a rate flow rate of 60 c.c./min.

As a result, 90% responses were obtained in 3 minutes to stepwise variations in the phenol concentration as shown in FIG. 2, with a rectilinear relation established between the phenol concentration and the detector output as seen in FIG. 3 in which a=17.1 ppm.

EXAMPLE 3

The concentration of hexane in rice oil was measured with use of a tube shaped from a porous material of ethylene tetrafluoride resin having channels extending therethrough. The hexane was used as a substitute for an odorous volatile component of the oil.

The following experiment was conducted in accordance with the principle shown in FIG. 1. Rice oil (500 c.c.) was placed into a 1-liter beaker and vigorously agitated by a magnetic stirrer at a constant temperature. The tube was immersed in the oil. Nitrogen gas was introduced into one end of the tube at constant pressure and at a constant flow rate, and the gas was withdrawn from the other end thereof and led to a flame ionization detector, the output of which was continuously recorded on a recorder.

For the experiment, rice oil containing a predetermined amount of hexane dissolved therein was prepared. Portions in a specified quantity of the rice oil were placed dropwise into the beaker at a given time interval to vary the hexane concentration of the rice oil stepwise to check the detector for response.

The tube had an inside diameter of 3.7 mm, a wall thickness of 500 $\mu$m, a pore size of 0.1 $\mu$m, a porosity of 30% and a length of 30 cm. The carrier gas, i.e. nitrogen gas, was passed through the tube at a flow rate of 60 c.c./min. There was little or no pressure difference between the gas and the rice oil.

Consequently the detector gave 90% responses in about 2 minutes to stepwise variations in the hexane concentration of the rice oil, thus revealing high responsiveness. A rectilinear relation was found between the hexane concentration and the detector output as seen in FIG. 3 wherein a=94 ppm. These results indicate that the method is fully useful for quantitative determination.

EXAMPLE 4

Figure 16:
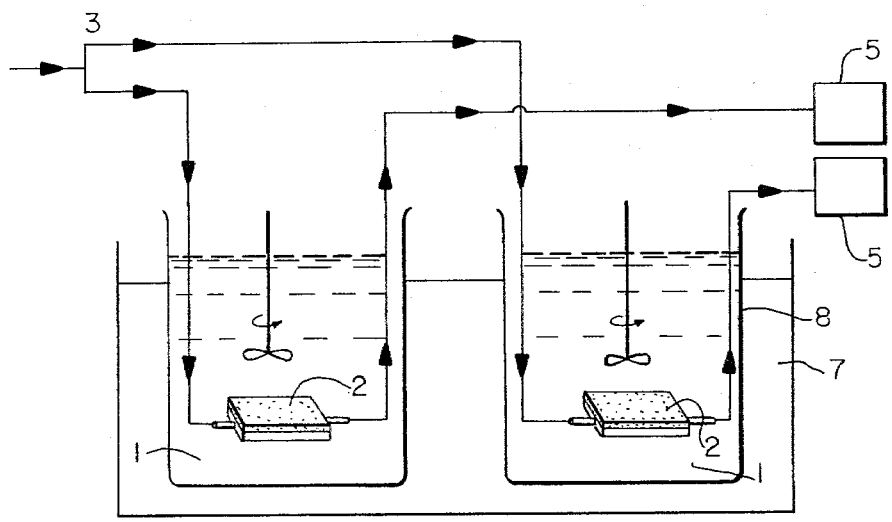
FIG. 16 is a diagram showing the apparatus used in Example 4.

As illustrated in FIG. 16, a first beaker 8 and a second beaker 8 were immersed in a constant-temperature bath 7. Polyethylene glycol 200 (indicated at 1) was contained in the beakers with stirring. A tube 2 comprising a hollow sampling container and a porous sheet of ethylene tetrafluoride resin attached to the open top side of the container was placed into each of the beakers. Nitrogen gas serving as a carrier gas was introduced into one end of each container through a supply pipe 3 at constant pressure and constant flow rate, with the other end of the container connected to each of the two flame ionization detectors, one of which was used as reference detector.

Ethanol dissolved in polyethylene glycol 200 was placed dropwise, in portions of predetermined quantity, into the first beaker at a specified time interval. The resulting output of the detector was recorded.

Since the flame ionization detector for the first beaker also detects the polyethylene glycol 200, the output from the second beaker containing the glycol alone was used as a blank. The difference in output between the two detectors was taken as the output corresponding to the ethanol concentration. Because polyethylene glycol has a low vapor pressure and accordingly a low concentration in the carrier gas, even a very low ethanol concentration was found to be satisfactorily detectable by this method.

The beaker had a capacity of 1,000 c.c. with 800 c.c. of the liquid placed therein at a temperature of 20° C. The carrier gas was fed at a flow rate of 60 c.c./min. There was little or no pressure difference between the gas and the liquid. The sheet measured 2.0 cm × 8.0 cm and had a thickness of 0.55 mm, a maximum pore size of 2.0 $\mu$m and a porosity of 62.0%.

Each portion of the ethanol added was adjusted to such an amount as to produce an increase of 150 ppm in the ethanol concentration of the liquid.

The flame ionization detector used was one attached to a gas chromatograph (Model GC-6A, product of Shimadzu Co., Ltd.).

The experiment gave 90% responses in about 50 seconds, with a rectilinear relation found between the detector output and the ethanol concentration.

EXAMPLE 5

The following experiment was conducted on a system for controlling the feed of main carbon source according to the process illustrated in FIG. 17, which shows a culture broth 1, a porous partition tube 2, a detector 5, a feed tank 9 and a moter controller 10.

*Saccharomyces cerevisiae* (baker's yeast) was used for cultivation with molasses serving as the main carbon source. Additionally ammonium sulfate and urea were used as nitrogen sources, and phosphoric acid as a phosphorus source. The culture broth was placed in a 30-liter jar fermenter as adjusted to a pH of 4.5 and to a temperature of 33° C., with air supplied at a rate of 20 Nl/min. with stirring at 500 r.p.m. The feed of molasses was started at an initial yeast concentration of 0.5% by dry weight.

The tube was liquid-repellent porous tube having channels extending through the wall thereof and was made of ethylene tetrafluoride resin. The tube was 20 cm in length and about 4 mm in inside diameter. Nitrogen gas was continuously passed through the tube at a flow rate of 60 ml/min. As the detector 5, a flame ionization detector was used. The output signal of the detector was fed via a converter to a pump mounted on the feed line. Thus the pump was intermittently driven automatically by the controller for the control of the main feed (molasses).

The system was set for automatic control so that the ethanol concentration of the culture broth would be maintained at 1,000 ppm, by driving the pump to feed molasses until the concentration reached to 1,050 ppm whenever the concentration was decreased to 950 ppm. Consequently the ethanol concentration of the broth was controlled to 900 to 1,100 ppm. The results of the experiment are given in FIG. 18, in which the culture time is plotted as abscissa vs. the ethanol concentration of the broth as ordinate.

Similar cultivation conducted by the usual intermittent sampling method entailed widely varying ethanol concentrations over the range of 1,000 to 3,000 ppm as illustrated in FIG. 19.

What we claim is:

1. A method of measuring the concentration of a gaseous or volatile substance in a liquid comprising the steps of immersing in the liquid a liquid-repellent porous partition tubing having pores with the pore sizes of 0.1 to 5 $\mu$m and minute channels extending through the wall of the tubing, passing a carrier gas through the partition tubing, leading the carrier gas to measuring means and detecting the quantity of the gaseous or volatile substance permeating through the tubing wall from the liquid and diffusing into the carrier gas to continuously or intermittently measure the concentration of the substance in the liquid.

2. A method as defined in claim 1 wherein the partition tubing is water-repellent.

3. A method as defined in claim 1 wherein the partition tubing is oil-repellent.

4. A method as defined in claim 1 wherein the partition tubing is made of ethylene tetrafluoride resin.

5. A method as defined in claim 1 wherein the liquid is an aqueous liquid.

6. A method as defined in claim 5 wherein the aqueous liquid is a culture broth for a microorganism.

7. A method as defined in claim 5 wherein the aqueous liquid is a fermentation or brewing liquid.

8. A method as defined in claim 5 wherein the aqueous liquid is industrial waste water.

9. A method as defined in claim 5 wherein the aqueous liquid is a suspension of polymer and oligomer.

10. A method as defined in claim 1 wherein the liquid is a nonaqueous liquid.

11. A method as defined in claim 10 wherein the nonaqueous liquid is a fluid oil or fat.

12. A method as defined in claim 1 wherein the carrier gas is nitrogen.

13. A method as defined in claim 1 wherein the carrier gas is helium.

14. A method as defined in claim 1 wherein the quantity of the gaseous or volatile substance diffused into the carrier gas is intermittently measured by gas chromatograph.

15. A method as defined in claim 1 wherein the quantity of the gaseous or volatile substance diffused into the carrier gas is detected by a flame ionization detector to continuously measure the concentration of the gaseous or volatile substance in the liquid.

16. An apparatus for sampling a gaseous or volatile substance in a liquid comprising a liquid-repellent porous partition tubing having pores with the pore sizes of 0.1 to 5 $\mu$m and minute channels extending through the wall of the partition tubing for permitting the gaseous or volatile substance to diffuse therethrough into a carrier gas in the partition tubing, the partition tubing having one end in communication with a carrier gas supply pipe and the other end in communication with a carrier gas discharge pipe extending to means for measuring the concentration of the gaseous or volatile substance.

17. An apparatus as defined in claim 16 wherein the partition tubing is made of ethylene tetrafluoride resin.

18. An apparatus as defined in claim 16 wherein the partition tubing is detachably connected to the carrier gas supply pipe and to the carrier gas discharge pipe.

19. An apparatus for sampling a gaseous or volatile substance in a liquid comprising a liquid-repellent porous partition tubing having pores with the pore sizes of 0.1 to 5 $\mu$m and minute channels extending through the wall of the partition tubing for permitting the gaseous or volatile substance to diffuse therethrough into a carrier gas in the partition tubing, the partition tubing having one end in communication with a carrier gas supply pipe and the other end in communication with a carrier gas discharge pipe extending to means for measuring the concentration of the gaseous or volatile substance, the carrier gas discharge pipe being provided with heating means.

20. An apparatus as defined in claim 19 wherein the heating means is a piping structure for passing water of elevated temperature therethrough.

21. An apparatus as defined in claim 19 wherein the heating means comprises an electric heating element.

22. An apparatus as defined in claim 20 or 21 wherein the heating means is covered with a heat insulating material.

23. An apparatus as defined in claim 20 or 21 wherein the heating means is covered with a synthetic resin layer over the outer periphery thereof.

24. An apparatus for sampling a gaseous or volatile substance in a liquid comprising a liquid-repellent porous partition tubing having pores with the pore sizes of 0.1 to 5 $\mu$m and minute channels extending through the wall of the partition tubing for permitting the gaseous or volatile substance to diffuse therethrough into a carrier gas in the partition tubing, the tubing having one end in communication with a carrier gas supply pipe and the other end in communication with a carrier gas discharge pipe extending to means for measuring the concentration of the gaseous or volatile substance, the carrier gas supply pipe including a tubular portion to be immersed in the liquid for exchanging heat with the liquid.

25. An apparatus as defined in claim 24 wherein the tubular portion is a metal pipe of small wall thickness.

* * * * *